(12) United States Patent
Ouchi (10) Patent No.: US 9,046,466 B2
(45) Date of Patent: Jun. 2, 2015

(54) X-RAY IMAGING APPARATUS

(75) Inventor: Chidane Ouchi, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 302 days.

(21) Appl. No.: 13/641,966

(22) PCT Filed: May 20, 2011

(86) PCT No.: PCT/JP2011/062149
§ 371 (c)(1),
(2), (4) Date: Oct. 18, 2012

(87) PCT Pub. No.: WO2011/149033
PCT Pub. Date: Dec. 1, 2011

(65) Prior Publication Data
US 2013/0034209 A1   Feb. 7, 2013

(30) Foreign Application Priority Data

May 27, 2010 (JP) ................. 2010-121225

(51) Int. Cl.
*G03H 5/00* (2006.01)
*G01N 23/20* (2006.01)
(Continued)

(52) U.S. Cl.
CPC .............. *G01N 23/04* (2013.01); *G02B 5/1838* (2013.01); *G02B 5/189* (2013.01); *G01J 9/00* (2013.01);
(Continued)

(58) Field of Classification Search
CPC ..... G21K 1/06; G21K 2207/005; G02B 5/18; G02B 5/1814; G02B 5/1838; G02B 5/1842; G02B 5/1866; G02B 5/1871; G02B 5/1885; G02B 5/189; G02B 2005/1804; G02B 27/4272; G01B 11/2518; G01B 11/2527; G01B 11/254; G01J 9/00; G01J 9/0215; G01J 2009/0219
USPC ............ 378/2, 36, 62, 70, 71, 82, 210; 359/1, 359/10, 11, 233, 577, 578, 896, 902, 197, 359/198; 356/457, 458, 900, 902, 903, 925
See application file for complete search history.

(56) References Cited

U.S. PATENT DOCUMENTS

| 7,180,979 B2 | 2/2007 | Momose ......................... 378/62 |
| 2009/0092227 A1* | 4/2009 | David et al. ..................... 378/36 |

(Continued)

FOREIGN PATENT DOCUMENTS

WO   WO 2006/131235 A   12/2006

OTHER PUBLICATIONS

D. Malacara, *Optical Shop Testing*, $2^{nd}$ ed., Chapter 14, pp. 501-532 (1992).

(Continued)

*Primary Examiner* — Anastasia Midkiff
(74) *Attorney, Agent, or Firm* — Fitzpatrick, Cella, Harper & Scinto (57) ABSTRACT

Provided is an X-ray imaging apparatus having simple configuration and obtaining differential phase contrast images in two directions crossing each other without rotating the diffraction grating and the masking grating. The apparatus including: a diffraction grating diffracting X-rays; a masking grating masking portions rays and transmitting portions are two-dimensionally arranged to partially mask bright zones of the interference pattern; a moving device changing the relative position between the interference pattern and the masking grating; a detector detecting the intensity distribution of the X-rays transmitted through the masking grating; and a calculator calculating a differential phase contrast image or a phase contrast image of a subject, the calculator being configured to calculate the differential phase contrast image or the phase contrast image in each of two mutually crossing directions on the basis of results of detection performed a plurality of times by the detector.

12 Claims, 7 Drawing Sheets

(51) Int. Cl.
*G01B 9/021* (2006.01)
*G03H 1/10* (2006.01)
*G01N 23/04* (2006.01)
*G01J 9/02* (2006.01)
*A61B 6/00* (2006.01)
*G02B 5/18* (2006.01)
*G01J 9/00* (2006.01)
*G21K 1/06* (2006.01)
*G01B 11/25* (2006.01)

(52) U.S. Cl.
CPC ............... *G02B 5/1871* (2013.01); *G21K 1/06* (2013.01); *G02B 5/1842* (2013.01); *G01J 9/0215* (2013.01); *G01B 11/2527* (2013.01); *G02B 5/18* (2013.01); *G02B 5/1814* (2013.01); *A61B 6/484* (2013.01); *G01N 2223/1016* (2013.01); *G01N 2223/32* (2013.01); *G21K 2201/06* (2013.01); *G21K 2207/005* (2013.01); *A61B 6/4291* (2013.01)

(56) References Cited

U.S. PATENT DOCUMENTS

| | | | |
|---|---|---|---|
| 2010/0091947 A1* | 4/2010 | Niu et al. | 378/63 |
| 2010/0177864 A1* | 7/2010 | Donath et al. | 378/16 |
| 2011/0235775 A1* | 9/2011 | Tada | 378/36 |
| 2012/0099702 A1* | 4/2012 | Engel et al. | 378/62 |
| 2012/0236988 A1 | 9/2012 | Den et al. | 378/36 |
| 2012/0263274 A1 | 10/2012 | Ouchi | 378/62 |
| 2012/0281217 A1 | 11/2012 | Ouchi et al. | 356/432 |
| 2013/0070895 A1* | 3/2013 | Ouchi | 378/62 |

OTHER PUBLICATIONS

M. Jiang et al., "X-Ray Phase-Contrast Imaging with 2D Grating Interferomerty", *Developments in X-Ray Tomography VI*, vol. 7078, pp. 707816-1-707816-11 (Aug. 12, 2008).

I. Zanette et al., "2D Grating Simulation for X-Ray Phase-Contrast and Dark-Field Imaging with a Talbot Interferimeter", *AIP Conference Proceedings American Institute of Physics USA*, vol. 1221, pp. 73-79 (Apr. 6, 2010).

D. Malacara, *Optical Shop Testing*, $2^{nd}$ ed., Chapter 14 (pp. 501-532), (Jan. 1, 1992).

* cited by examiner

X-RAY IMAGING APPARATUS

TECHNICAL FIELD

The present invention relates to an X-ray imaging apparatus for measuring an X-ray phase contrast image of a subject.

BACKGROUND ART

When X-rays are transmitted through a subject, the phase of the X-rays is changed due to the constituent elements and the difference in density of the subject. The research of the phase contrast imaging method using the phase change of the X-rays has been conducted since the 1990s. One of the phase contrast imaging methods is described in Patent Document 1. The method is a kind of a method referred to as a phase stepping method. The phase stepping method is featured in that the method is influenced by neither the transmittance distribution of the subject nor the spatial ununiformity of the intensity of X-rays irradiated onto the subject and has a high spatial resolution which is in principle the same as the resolution of an imaging element used to capture the image of the X-rays.

Patent Document 1 proposes an X-ray imaging apparatus as described below. In the apparatus, X-rays transmitted through a subject are irradiated onto a diffraction grating so that a periodic interference pattern referred to as a self-image is formed at a position away from the diffraction grating by a specific distance (Talbot distance). Further, in the apparatus, in order to generate a moiré, a masking grating having the same period as the period of the interference pattern is provided at the position where the interference pattern is formed, and the generated moiré is detected by an X-ray detector. Further, the apparatus is configured such that the phase information of the X-rays transmitted through the subject is acquired on the basis of three or more moiré images detected by moving the diffraction grating or the masking grating at a constant interval, and such that a phase contrast image of the subject is obtained from the phase information.

CITATION LIST

Patent Literature

PTL 1: U.S. Pat. No. 7,180,979
PTL 2: International Publication No. WO2006/131235

SUMMARY OF INVENTION

Technical Problem

In general, in order to reconstruct the phase contrast image of the subject, it is necessary to obtain differential phase contrast images in two directions crossing each other. In order to obtain the differential phase contrast images in two directions crossing each other by the method proposed by PTL 1, it is necessary that, after a moiré image is captured as described above, the diffraction grating and the masking grating are rotated in the grating surface, and then another moiré image is captured. However, in the case where the diffraction grating and the masking grating are rotated in this way, the structure of the imaging apparatus becomes complicated. Further, in addition to the operation for capturing the moiré image, the operation for rotating the diffraction grating and the masking grating is required, and hence the operation of the imaging apparatus also becomes complicated.

In view of the above, the present invention is to provide an X-ray imaging apparatus which has a simpler configuration than that of the prior art apparatus and which can obtain differential phase contrast images in two directions crossing each other without rotating the diffraction grating and the masking grating.

Solution to Problem

In view of the above problem, An X-ray imaging apparatus according to the present invention includes: a diffraction grating which diffracts X-rays emitted from an X-ray source to thereby form an interference pattern having two-dimensionally arranged bright and dark zones; a masking grating in which masking portions for masking the X-rays and transmitting portions for transmitting the X-rays are two-dimensionally arranged to partially mask each of the bright zones of the interference pattern; a moving device which changes the relative position between the interference pattern and the masking grating; a detector which detects the intensity distribution of the X-rays transmitted through the masking grating; and a calculator which calculates a differential phase contrast image or a phase contrast image of a subject on the basis of the result of detection performed by the detector, the calculator being configured to calculate the differential phase contrast image or the phase contrast image in each of two mutually crossing directions on the basis of results of detection performed a plurality of times by the detector.

Advantageous Effects of Invention

According to the present invention, it is possible to provide an X-ray imaging apparatus which has a simpler configuration than that of the prior art apparatus and which can obtain differential phase contrast images in two directions crossing each other without rotating the diffraction grating and the masking grating.

Further features of the present invention will become apparent from the following description of exemplary embodiments with reference to the attached drawings.

DESCRIPTION OF EMBODIMENTS

An exemplary embodiment according to the present invention will be described with reference to FIG. 1. An imaging apparatus illustrated in FIG. 1 includes: an X-ray source 1 which emits X-rays; a diffraction grating 4 which diffracts X-rays emitted from the X-ray source 1 to form an interference pattern having two-dimensionally arranged bright and dark zones; a moving device 5 for diffraction grating which changes the position of the diffraction grating 4 in the grating surface of the diffraction grating 4; a masking grating 6 in which transmitting portions for transmitting X-rays and masking portions for masking X-rays are two-dimensionally arranged; a moving device 7 for masking grating which changes the position of the masking grating 6 in the grating surface of the masking grating 6; an X-ray detector 8 which acquires the intensity distribution of X-rays transmitted through the masking grating 6; and a calculator 9 which calculates a differential phase contrast image or a phase contrast image of a subject from the detection result of X-ray intensity distribution acquired by the X-ray detector 8. Note that the moving device 5 for diffraction grating and the moving device 7 for masking grating are moving device for changing the relative position between the interference pattern and the masking grating 6, and hence it is not always necessary to provide both the moving devices. Further, when the relative position between the interference pattern and the masking grating 6 can be moved by, for example, a moving device for X-ray source for moving the X-ray source, neither the moving device 5 for diffraction grating nor the moving device 7 for masking grating need to be provided.

PTL 2 discloses the method of moving an X-ray source for band scanning, which can also be applied to the present invention, and hence detailed explanations thereof is omitted. In principle, an X-ray source is moved to an opposite direction of the movement of the interference pattern. Then, a movement distance of the interference pattern on a diffraction gratings is derived by multiplying the movement distance of the X-ray source by an amount derived when the distance between the diffraction gratings and a masking portion is divided by the distance between the X-ray source and the diffraction gratings.

In the following, the above-described configuration will be described in detail. As the diffraction grating 4, it is possible to use a phase type diffraction grating in which phase advance portions and phase lag portions are two-dimensionally and periodically arranged, or an amplitude type diffraction grating in which masking portions and transmitting portions are two-dimensionally and periodically arranged. A phase type diffraction grating according to the present embodiment has a structure in which the thickness of the X-ray transmitting member is periodically changed so that a fixed amount of phase shift is produced between the phase of the X-ray transmitted through the phase advance portion and the phase of the X-ray transmitted through the phase lag portion.

When X-rays 2 emitted from the X-ray source 1 are incident on the diffraction grating 4, an interference pattern, in which bright zones and dark zones are two-dimensionally arranged, is formed at a position away from the diffraction grating by a predetermined distance (Talbot distance) expressed by $Z_1$ of Expression (1).

$$\frac{1}{Z_0} + \frac{1}{Z_1} = \frac{1}{N}\frac{\lambda}{d^2} \qquad \text{Expression (1)}$$

Here, in Expression (1), $Z_0$ represents the distance between the X-ray source 1 and the diffraction grating 4, $\lambda$ represents the wavelength of X-ray 2, and d represents the grating period of the diffraction grating 4. Further, in the case where the amount of phase shift is $\pi/2$ and where the diffraction grating is a phase type diffraction grating in which the phase advance portions and the phase lag portions are arranged in a checker pattern, N is a real number expressed by $n-1/2$, while in the case where the amount of phase shift is $\pi$ and where the diffraction grating is a phase type diffraction grating in which the phase advance portions and the phase lag portions are arranged in a checker pattern, N is a real number expressed by $n/2-1/4$. Further, in the case where the diffraction grating is the amplitude type diffraction grating in which the masking portions and the transmitting portions are arranged in a checker pattern, N is a real number expressed by n. In the above expressions, n is a natural number.

In the masking grating 6, the masking portions for masking X-rays and the transmitting portions for transmitting X-rays are two-dimensionally arranged. The masking grating 6 is arranged at the position where the interference pattern is formed, and partially masks of each of the bright zones of the interference pattern by each of the masking portions. The period of the masking grating 6 of the present embodiment is set to coincide with the period of the interference pattern in the state where a subject 3 does not exist, and the direction of the period of the masking grating 6 is also set to coincide with the direction of the period of the interference pattern.

The moving device 5 for diffraction grating has a driving device to move the diffraction grating 4 in the direction of the period of the diffraction grating 4. When the diffraction grating 4 is moved by the moving device 5 for diffraction grating, the interference pattern is also moved. When the interference pattern is moved, the relative position between the interference pattern and the masking grating 6 is changed, so that the amount of X-rays transmitted through the respective transmitting portions of the masking grating 6 is periodically changed.

Similarly, the moving device 7 for masking grating has a driving device to move the masking grating 6 in the direction of the period of the masking grating 6. When the masking grating 6 is moved, the relative position between the interference pattern and the masking grating 6 is changed, so that the amount of X-rays transmitted through the respective transmitting portions of the masking grating 6 is periodically changed.

The detector 8 detects, a plurality of times, the intensity distribution of X-rays transmitted through the masking grating in correspondence with the change in the relative position between the interference pattern and the masking grating 6, which change is produced by the moving device 5 for diffraction grating or the moving device 7 for masking grating.

Further, the calculator 9 calculates a differential phase contrast image in each of the mutually-crossing two directions on the basis of the results of detection performed the plurality of times by the detector 8, and calculates a phase contrast image by integrating the differential phase contrast image. The method of calculation of the phase contrast image of the subject performed by calculator 9 will be described below.

Figure 1:
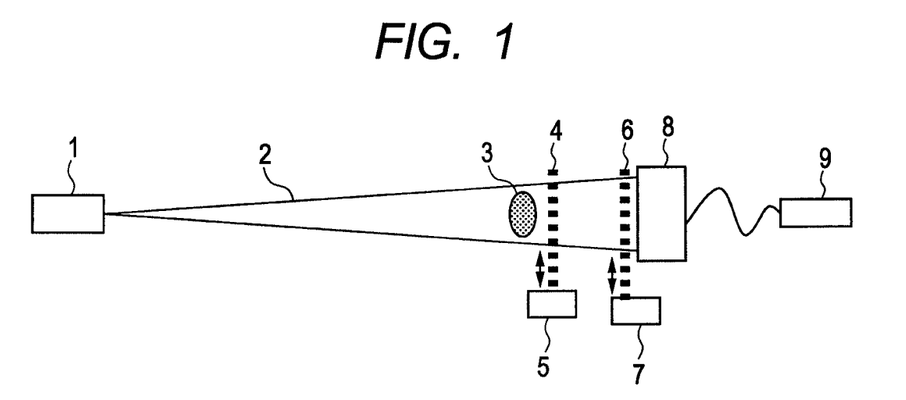
FIG. 1 is a diagram for describing a configuration example of an X-ray imaging apparatus according to Exemplary embodiment 1.

In FIG. 1, the subject 3 is arranged between the X-ray source 1 and the diffraction grating 4. However, it may also be arranged between the diffraction grating 4 and the masking grating 6. When the subject 3 exists between the X-ray source 1 and the diffraction grating 4 or between the diffraction grating 4 and the masking grating 6, the positions, at which the bright zones and the dark zones of the interference pattern are respectively formed, are changed according to the refractive index distribution of the subject. The reason for this will be described briefly below.

When the phase of an X-ray transmitted through the subject 3 is changed according to the refractive index distribution of the subject 3, the differential phase which is the spatial change rate of the phase of the X-ray is also changed. Since the traveling direction of the X-ray is changed in proportion to the differential phase of the X-ray, the positions of the bright and dark zones of the interference pattern on the masking grating 6 are also changed in proportion to the distribution of the differential phase.

When the x-direction differential phase of the X-ray transmitted through the subject 3 is defines as $\phi_x$, the change of the traveling direction of the X-ray is obtained as $\lambda \phi_x/(2\pi)$. Thus, when the positional change of the interference pattern in the x direction is defined as $\Delta x$, the positional change $\Delta x$ is given by $\Delta x = \lambda \phi_x \times Z_1/(2\pi)$. Therefore, when the positional change $\Delta x$ of the interference pattern in the x direction is measured, the x-direction differential phase of the X-ray transmitted through the subject can be obtained from the relationship expressed by Expression (2). The differential phase $\phi_x$ is referred to as a differential phase contrast image of the subject in the x direction.

$$\phi_x = \frac{2\pi}{\lambda} \frac{\Delta x}{Z_1} \quad \text{Expression (2)}$$

The method for obtaining $\Delta x$ will be described below. One of the diffraction grating 4 and the masking grating 6 is moved, by corresponding one of the moving device 5 and the moving device 7, in one direction in the grating surfaces of the one of the diffraction grating 4 and the masking grating 6, so that the relative position between the interference pattern and the masking grating 6 is changed in the one direction at an equal interval. In this case, the intensity distribution of the X-rays transmitted through the masking grating 6 is detected by the X-ray detector 8 at least at three relative positions corresponding to the changes in the relative position between the masking grating 6 and the interference pattern.

Next, when calculation processing based on an algorithm of the phase stepping method is performed by the calculator 9 by using the results of the plural detection, the positional change $\Delta x$ of the interference pattern in the x direction can be calculated. Thus, the differential phase contrast image in each of two mutually crossing directions can be obtained in such a manner that the relative position between the interference pattern and the masking grating is changed in the direction crossing the x direction so that the intensity distribution of the X-rays is detected at least three relative positions corresponding to the changes in the relative position, and that the calculation processing based on the detection results is performed. Even when the two mutually crossing directions are not orthogonal to each other, the two-dimensional differential phase contrast image or phase contrast image of the subject can be obtained. However, when the detection is performed in the two directions which are not orthogonal to each other, the calculation processing for obtaining the two-dimensional differential phase contrast image or phase contrast image generally becomes complicated. In the present embodiment, differential phase contrast images in two directions orthogonal to each other are obtained in such a manner that the relative position between the interference pattern and the masking grating 6 is moved by moving the diffraction grating 4 or the masking grating 6 in the two directions orthogonal to each other, that the intensity distribution of X-rays is detected by the detector 8 in correspondence with the movement of the relative position, and that the differential phase contrast image in each of the two orthogonal directions is calculated by the calculator 9.

As described above, the period of the masking grating 6 is made to coincide with the period of the interference pattern formed on the masking grating in the state where the subject 3 does not exist between the X-ray source 1 and the diffraction grating 4 or between the diffraction grating 4 and the masking grating 6. Also, the direction of the period of the masking grating 6 is made to coincide with the direction of the period of the interference pattern. Therefore, when the subject 3 does not exist, the relative positions $x_0$ between the respective transmitting portions of the masking grating 6 and the respective bright zones of the interference pattern are equal to each other over the entire area of the interference pattern.

It is seen from Expression (2) that, even when the positional change $\Delta x$ is changed by a value fixed over the entire area of the interference pattern, the shape of the differential phase of X-ray is not changed. The measurement in the state where the subject 3 does not exist does not necessarily need to be performed in order to obtain the phase contrast image. However, in order to eliminate the influences of the shape error, the arrangement error, and the like, of the diffraction grating 4 and the masking grating 6, it is effective to perform the measurement in the state where the subject 3 does not exist. That is, when the differential phase change, obtained by subtracting the differential phase of an X-ray measured in the state where the subject 3 does not exist from the differential phase of an X-ray measured in the state where the subject 3 exist, is used as the differential phase change of the X-ray caused by the subject 3, the period and the direction of the period of the masking grating 6 may not strictly coincide with that of the interference pattern. Further, even when there is an error in the pattern shape of the diffraction grating 4 and the masking grating 6, it is possible to eliminate the influence of the error.

Note that the detailed description of the phase stepping method and its algorithm is omitted here because they are described in many books about interferometers, for example, in Chapter 14 (page 501) of second edition of "Optical Shop Testing" by Daniel Malacara. In order to obtain the phase contrast image of the subject, the differential phase contrast image of the subject may only be integrated in the differential direction.

As described above, according to the exemplary embodiment, by using a phase stepping method, differential phase contrast images in two mutually crossing directions can be obtained without exchanging the diffraction grating or changing the attaching direction of the diffraction grating. Further, the differential phases in the two directions can be calculated by commonly using one detection result, and hence the number times of the detection of the X-ray intensity distribution can be reduced by one.

EXAMPLES

In the following, examples of the present invention will be described.

Example 1

Example 1 according to the present invention 1 will be described with reference to FIG. 1 to FIG. 7. Similarly to the X-ray imaging apparatus of the exemplary embodiment, an X-ray imaging apparatus of Example 1 has the configuration illustrated in FIG. 1, in which X-rays emitted from the X-ray source is transmitted through the subject, the diffraction grating, and the masking grating, so as to reach the X-ray detector. Further, the relative position between the interference pattern and the masking grating is changed by the moving device for diffraction grating, and the position of the masking grating is fixed.

Figure 2:
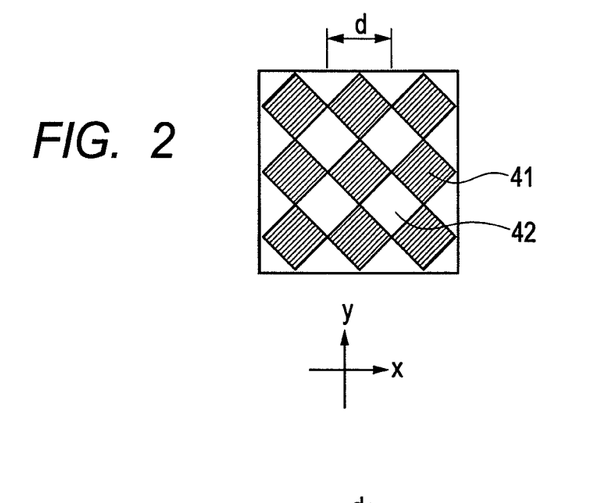
FIG. 2 is a diagram for describing a diffraction grating of an X-ray imaging apparatus in Example 1.

FIG. 2 is a view of a part of the diffraction grating 4 in the present example seen from the side of the X-ray source. In the present example, a phase type diffraction grating made of silicon and formed by arranging phase advance portions 41 and phase lag portions 42 in a checker pattern is used as the diffraction grating. The phase advance portion 41 and the phase lag portion 42 have a difference in the thickness of silicon so that the phase difference between the X-ray transmitted through the phase advance portion 41 and the X-ray transmitted through the phase lag portion 42 becomes $\pi/2$, and are arranged with a period d.

The masking grating is arranged such that the interval $Z_0$ between the diffraction grating and the masking grating satisfies Expression (1) so that an interference pattern is formed on the masking grating. Here, N is set as N=1/2.

Figure 3:
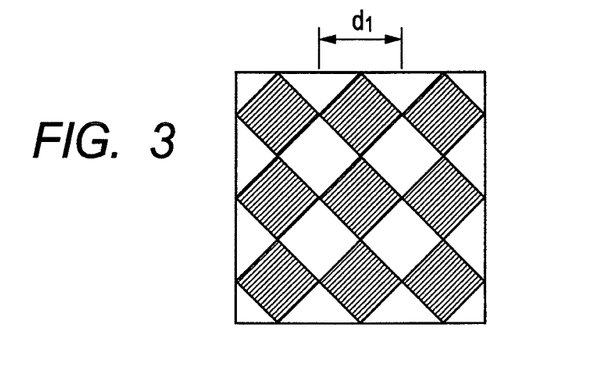
FIG. 3 is a diagram for describing an interference pattern in Example 1.

FIG. 3 illustrates the interference pattern formed on the masking grating when the diffraction grating of the present example is used, and the period $d_1$ of the interference pattern is expressed by Expression (3).

$$d_1 = \frac{Z_0 + Z_1}{Z_0} d \quad \text{Expression (3)}$$

Figure 4:
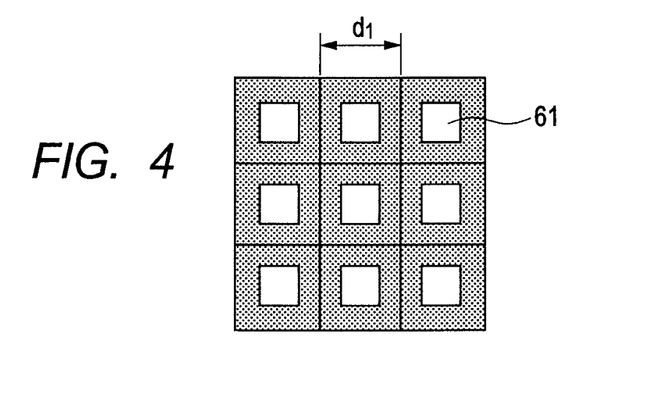
FIG. 4 is a diagram for describing a masking grating in Example 1.

Here, as described before, $Z_1$ is the interval between the X-ray source and the diffraction grating. FIG. 4 is a view of a part of the masking grating in the present example seen from the side of the X-ray source. The masking grating is made of gold having a small transmittance to X-rays, and has transmitting portions 61 for transmitting the X-ray which are arranged in a mesh pattern at the same period $d_1$ as the period of the interference pattern. The transmitting portion 61 has a square shape having one side of $d_1/2$.

Figure 5A:
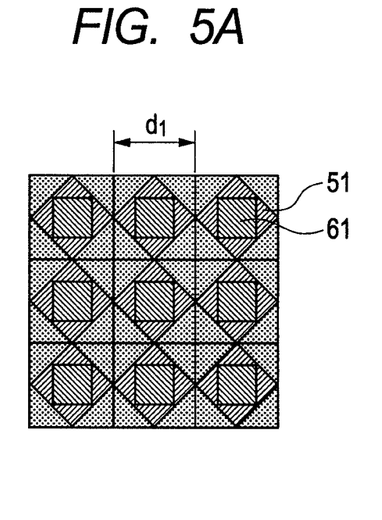
FIG. 5A is a diagram for describing a state where the interference pattern and the masking grating overlap with each other in Example 1.
Figure 5B:
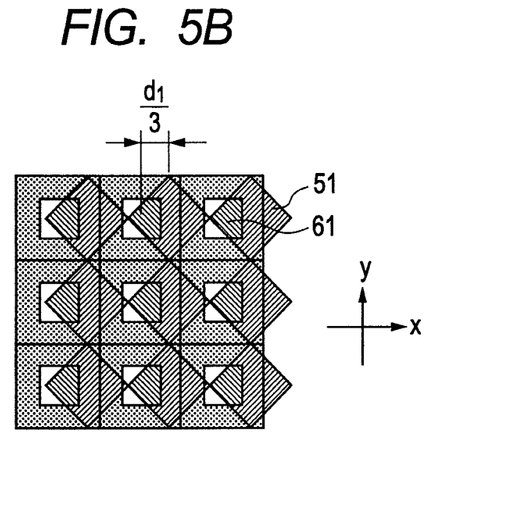
FIG. 5B is a diagram for describing a state where the interference pattern and the masking grating overlap with each other in Example 1.

In FIG. 5A and FIG. 5B which illustrate the masking grating and the interference pattern, the X-rays of only the portions of the bright zones 51 of the interference pattern, which portions respectively overlap with the transmitting portions 61 of the masking grating, are transmitted through the masking grating to reach the X-ray detector. The X-ray detector is configured by a CCD (Charge Coupled Device) imaging device having an X-ray luminescent material in the light receiving surface thereof. In the present example, the pixel size of the X-ray detector is set to be equal to the period $d_1$ of the masking grating, but may be set to be an integer multiple of $d_1$.

When the diffraction grating is moved in the surface of the diffraction grating by the moving device, the bright zones 51 of the interference pattern are also moved. FIG. 5B exemplarily illustrates an overlapping state between the bright zones 51 of the interference pattern and the transmitting portions 61 of the masking grating when the diffraction grating is moved in the x direction by a distance of 1/3 period, that is, a distance of $d_1/3$, from the position illustrated in FIG. 5A. In this example, the overlapping area between the bright zones 51 of the interference pattern and the transmitting portions 61 of the masking grating in the state illustrated in FIG. 5B is smaller as compared with the state illustrated in FIG. 5A, and hence the amount of the X-rays reaching the X-ray detector is also reduced.

Figure 6:
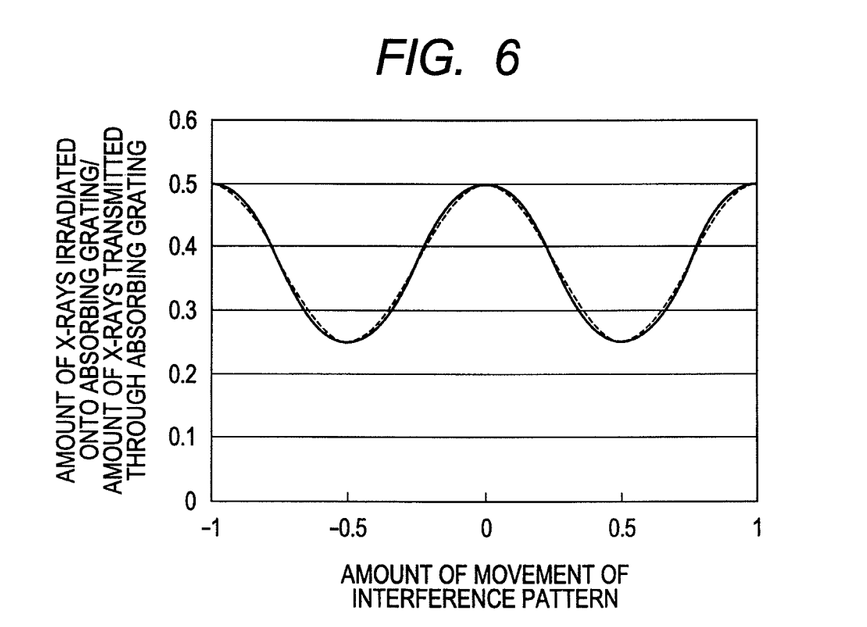
FIG. 6 is a diagram for describing a relationship between the amount of movement of the interference pattern and the amount of X-rays transmitted through the transmitting portions of the masking grating in Example 1.

FIG. 6 illustrates a relationship between the amount of movement of the interference pattern and the amount of X-rays transmitted through the masking grating. The solid line represents the ratio of the amount of X-rays transmitted through the masking grating to the amount of X-rays irradiated onto the masking grating, and the horizontal axis represents the amount of movement of the interference pattern with the period of the interference pattern as a unit. The dotted line represents, for comparison, an ideal sinusoidal wave whose amplitude, period, and phase are made to coincide with those of the waveform represented by the solid line. The change in the amount of X-rays transmitted through the transmitting portion 61 with respect to the amount of movement of the diffraction grating approximately coincides with the sinusoidal wave. Thus, even when a small number of steps (small number of times of detection) are adopted in the algorithm of the phase stepping method, the precision is not significantly degraded.

In the present example, three steps which are the minimum number of steps are used in consideration of the measuring time and the X-ray exposure dose to the subject, and an algorithm (three step algorithm) corresponding to the number of steps is adopted.

Figure 7:
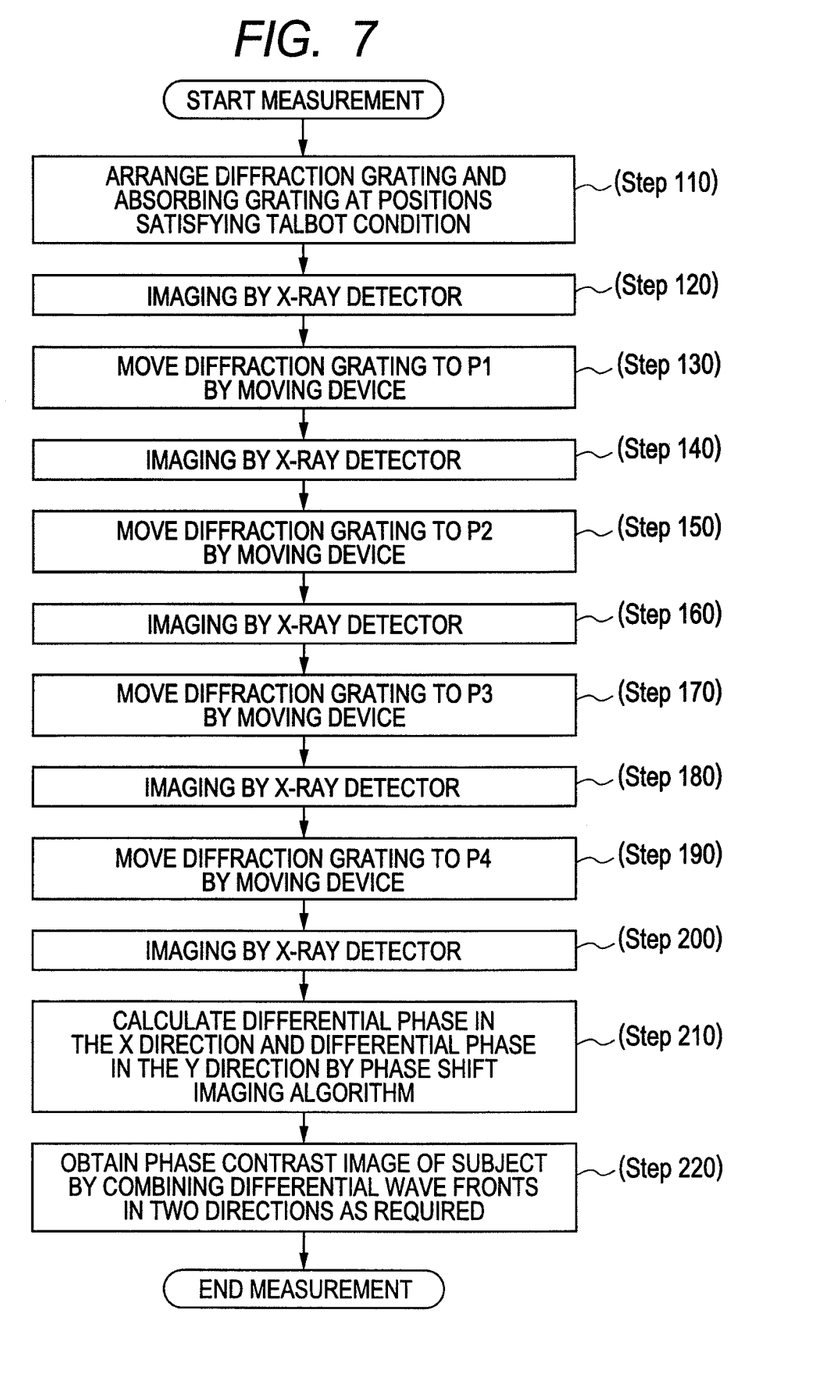
FIG. 7 is a diagram illustrating measurement steps in Example 1.

FIG. 7 illustrates the steps for measuring the subject in the present example. In step 110, the masking grating is arranged so that the distance $Z_1$ between the masking grating and the diffraction grating satisfies Expression (1), and hence an intensity distribution of a clear interference pattern is formed on the masking grating 6. In step 120, the intensity distribution is acquired with the detector, and the acquired intensity distribution is set to $I_0$. Here, in order to facilitate description, positions of $P_0$ to $P_4$ are defined as the positions of the diffraction grating 4 as follows. That is, the position of the diffraction grating in step 120 is set to $P_0$. Then, the position away from $P_0$ in the x direction by 1/3 period of the diffraction grating is set to $P_1$, and the position away from $P_0$ in the $-x$ direction by 1/3 period is set to $P_2$. Further, the position away from $P_0$ in the y direction by 1/3 period is set to $P_3$, and the position away from $P_0$ in the $-y$ direction by 1/3 period is set to $P_4$. Note that the x direction and the y direction are the directions respectively illustrated by the arrows in FIG. 2, and the $-x$ direction and the $-y$ direction are respectively correspond to directions reverse to the directions of the arrows illustrated in FIG. 2.

In step 130, the diffraction grating is moved to $P_1$ by the moving device for diffraction grating. In step 140, the intensity distribution is detected by the detector, and the detected intensity distribution is set to $I_1$. Subsequently, the movement of the diffraction grating 4 to $P_2$, $P_3$ and $P_4$ (in step 150, step 170 and step 190) and the detection of the intensity distribution (in step 160, step 180 and step 200) are repeated, and the obtained detection results are successively set to $I_2$, $I_3$ and $I_4$.

In step 210, by using Expression (4) and Expression (5) based on the three step algorithm of the phase stepping method, the phase $\phi_x$ as the differential phase in the x direction is calculated for each pixel from $I_0$, $I_1$ an $I_2$, and similarly, the phase $\phi_y$ as the differential phase in the y direction is calculated for each pixel from $I_0$, $I_3$ an $I_4$.

$$\varphi_x = \tan^{-1}\left(\frac{\sqrt{3}\,(-I_1+I_2)}{-I_1+2I_0-I_2}\right) \quad \text{Expression (4)}$$

$$\varphi_y = \tan^{-1}\left(\frac{\sqrt{3}\,(-I_3+I_4)}{-I_3+2I_0-I_4}\right) \quad \text{Expression (5)}$$

The phase $\phi_x$ and the phase $\phi_y$ calculated by using Expression (4) and Expression (5) are wrapped phases which are wrapped in the interval between 0 and $2\pi$, and hence are subjected to phase unwrapping so that the differential phases $W_x$ and $W_y$ in the respective directions are obtained. Further, as required, the phase distribution of the X-rays transmitted through the subject, that is, the phase contrast image of the subject can be obtained by combining two phase distributions obtained by integrating the differential phases in the two orthogonal directions obtained in step 220.

In the above description, the diffraction grating is moved in each of the positive and negative directions of each of the x and y directions by 1/3 period by using the position for the first time photographing as the center, but the amount of movement of the diffraction grating is not limited to this. However, in order to accurately obtain the differential phase contrast image or the phase contrast image of the subject, it is preferred that the respective amounts of movement are equal to each other. The phase $\phi_x$ and the phase $\phi_y$ can be calculated by adopting expressions based on the amounts of movement in place of Expression (4) and Expression (5). Further, as for the method for moving the diffraction grating, three or more grating positions may only be linearly arranged in both the x and y directions, and hence, for example, a method may also be adopted in which the diffraction grating is moved twice in the x direction from the initial position $P_0$ and then moved twice in the y direction.

Example 2

Example 2 of an X-ray imaging apparatus embodying the present invention will be described with reference to FIGS. 8A, 8B and 8C, FIG. 9 and FIG. 10. In the present example, the diffraction grating and the masking grating are different from those in the Example 1, and the other configuration is the same as that of Example 1.

Figure 8A:
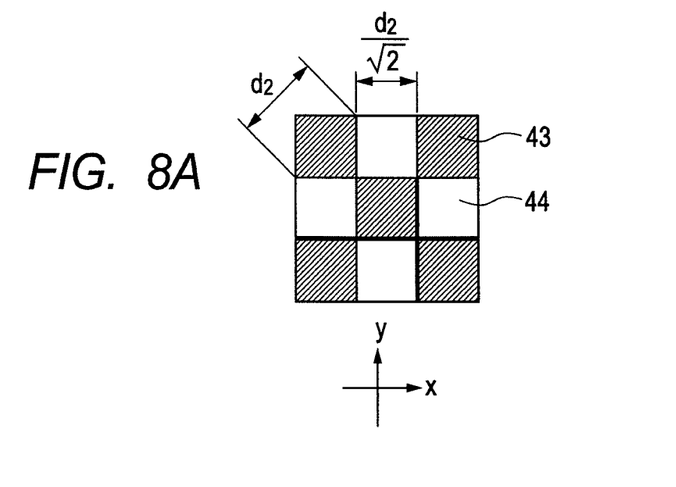
FIG. 8A is a diagram for describing a diffraction grating of an X-ray imaging apparatus in Example 2.
Figure 8B:
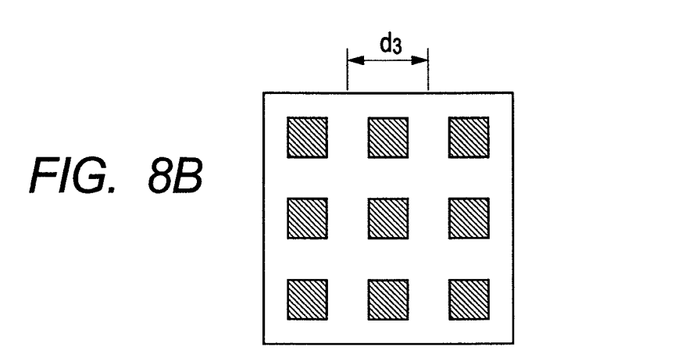
FIG. 8B is a diagram for describing an interference pattern in Example 2.

FIG. 8A is a view of a part of the diffraction grating 4 in the present example seen from the side of the X-ray source. A phase modulation grating made of silicon and formed by arranging phase advance portions 43 and phase lag portions 44 in a checker pattern with a period $d_2$ is used as the diffraction grating of the present example. The phase advance portions 43 and the phase lag portions 44 have a difference in the thickness of silicon so that the phase difference between the X-ray transmitted through the phase advance portion 43 and the X-ray transmitted through the phase lag portion 44 becomes $\pi$. The masking grating is arranged such that the interval $Z_0$ between the diffraction grating and the masking grating satisfies Expression (1) so that an interference pattern is formed on the masking grating. Here, N is set as N=1/4. FIG. 8B illustrates the interference pattern formed on the masking grating when the diffraction grating of the present example is used, and the period $d_3$ of the interference pattern is expressed by Expression (6).

$$d_3 = \frac{Z_0 + Z_1}{Z_0} \cdot \frac{d_2}{\sqrt{2}} \quad \text{Expression (6)}$$

Here, as described before, $Z_0$ is the interval between the X-ray source and the diffraction grating.

Figure 8C:
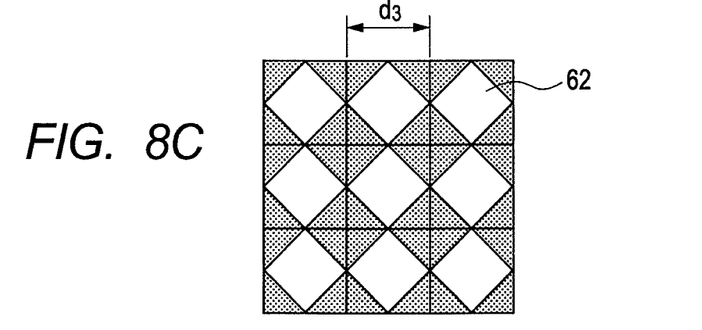
FIG. 8C is a diagram for describing a masking grating in Example 2.

FIG. 8C is a view of a part of the masking grating in the present example seen from the side of the X-ray source. The masking grating is made of gold similarly to Example 1, and has transmitting portions 62 arranged in a checker pattern with the same period $d_3$ as the period of the interference pattern. The transmitting portion 62 has a square shape having one side of $d_3/\sqrt{2}$.

Figure 9A:
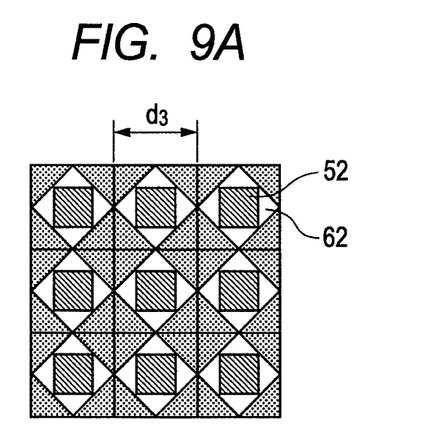
FIG. 9A is a diagram for describing a state where the interference pattern and the masking grating overlap with each other in Example 2.
Figure 9B:
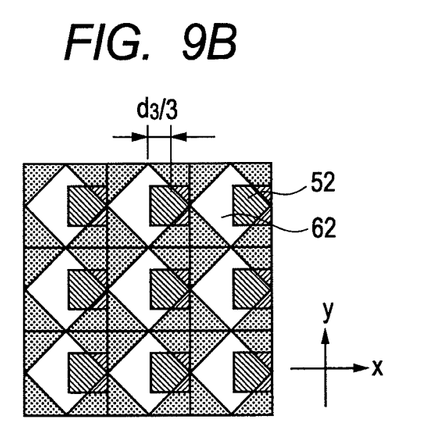
FIG. 9B is a diagram for describing a state where the interference pattern and the masking grating overlap with each other in Example 2.

In FIG. 9A and FIG. 9B which illustrate the interference pattern on the masking grating, only the portions of the bright zones 52 of the interference pattern, which portions respectively overlap with the transmitting portions 62, are transmitted through the masking grating to reach the X-ray detector. Similarly to Example 1, the pixel size of the X-ray detector is set to be equal to the period $d_3$ of the masking grating, but may be set to be an integer multiple of $d_3$.

In the present example, the relative position between the interference pattern and the masking grating is moved by moving the diffraction grating in the surface of the diffraction grating. FIG. 9B exemplarily illustrates an overlapping state between the interference pattern 52 and the masking grating 62 when the relative position between the interference pattern and the masking grating is moved in the x direction by a distance of 1/3 period of the interference pattern from the position illustrated in FIG. 9A. The area of the bright zone 52 of the interference pattern which overlaps with the transmitting portion 62 is changed according to the movement of the diffraction grating. In this example, the area of the bright zone 52 which overlaps with the transmitting portion 62 is reduced in the case illustrated in FIG. 9B as compared with the case illustrated in FIG. 9A, and hence the amount of X-rays reaching the X-ray detector is also reduced.

Figure 10:
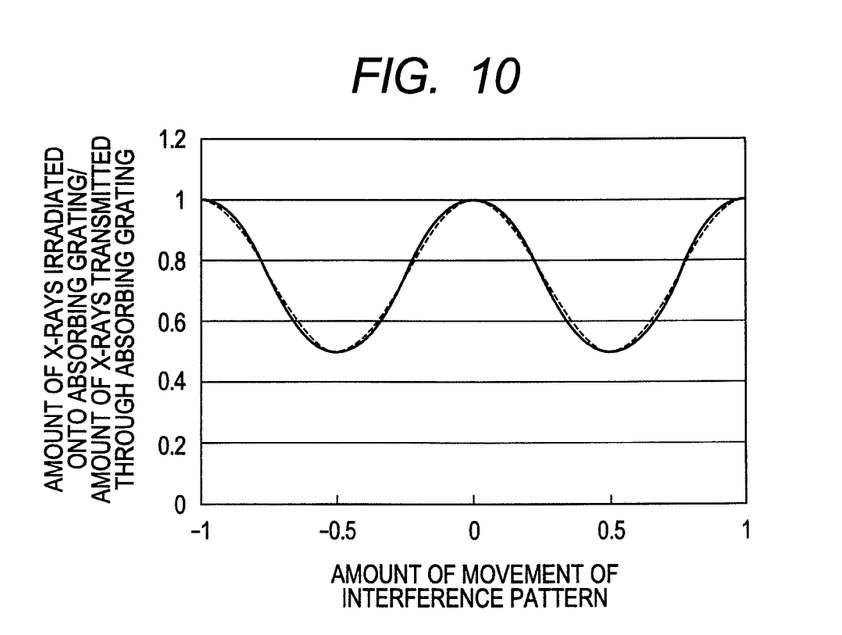
FIG. 10 is a diagram for describing a relationship between the amount of movement of the interference pattern and the amount of X-rays transmitted through the transmitting portions of the masking grating in Example 2.

FIG. 10 illustrates a relationship between the amount of movement of the interference pattern and the amount of X-rays transmitted through the transmitting portion 62 similarly to FIG. 6 in Example 1. The solid line represents the ratio of the amount of X-rays transmitted through the masking grating to the amount of X-rays irradiated onto the masking grating, and the horizontal axis represents the amount of movement of the interference pattern with the period of the interference pattern as a unit. The dotted line represents, for comparison, an ideal sinusoidal wave whose amplitude, period, and phase are made to coincide with those of the waveform represented by the solid line.

Similarly to Example 1, in the present example, the change in the amount of X-rays transmitted through the transmitting portion 61 with respect to the amount of movement of the diffraction grating also approximately coincides with the sinusoidal wave. Thus, even when a small number of steps are adopted in the algorithm of the phase stepping method, the precision is not significantly degraded. Also in the present example, the number of steps is set to 3.

As can be seen from the comparison between FIG. 10 and FIG. 6, the amount of X-rays transmitted through the masking grating 6 in the present example is twice the amount of the X-rays in Example 1. Therefore, the present example has a higher utilization efficiency of X-rays than that in Example 1. The measurement steps in the present example are the same as those in Example 1 described with reference to FIG. 7, and hence the description thereof is omitted.

Example 3

Example 3 according to the present invention will be described with reference to FIG. 11A, FIG. 11B and FIG. 11C. The present example is an X-ray imaging apparatus in which an amplitude type diffraction grating is used as the diffraction grating, and the other configuration is the same as that of Example 1.

Figure 11A:
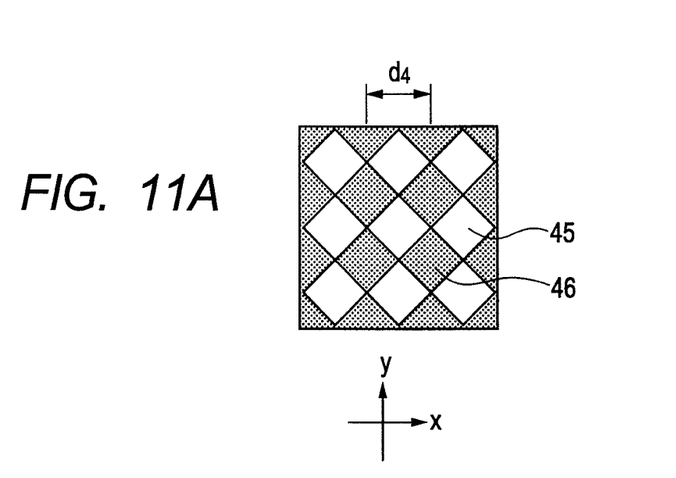
FIG. 11A is a diagram for describing a diffraction grating of an X-ray imaging apparatus in Example 3.

FIG. 11A is a view of a part of the diffraction grating in the present example seen from the side of the X-ray source. The diffraction grating used in the present example has a structure in which transmitting portions 45 for transmitting X-rays and masking portions 46 for masking X-rays are arranged in a checker pattern with a period of $d_4$. The masking grating is arranged such that the interval $Z_0$ between the diffraction grating and the masking grating satisfies Expression (1) so that an interference pattern is formed on the masking grating. Here, N is set as N=1.

Figure 11B:
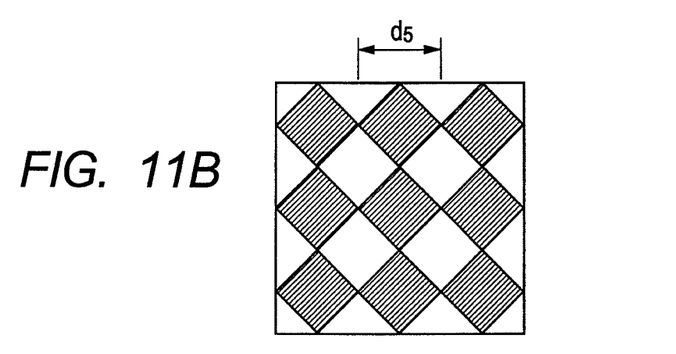
FIG. 11B is a diagram for describing an interference pattern in Example 3.

FIG. 11B illustrates the interference pattern formed on the masking grating, and the period $d_5$ of the interference pattern is expressed by Expression (7).

$$d_5 = \frac{Z_0 + Z_1}{Z_0} d_4 \quad \text{Expression (7)}$$

Figure 11C:
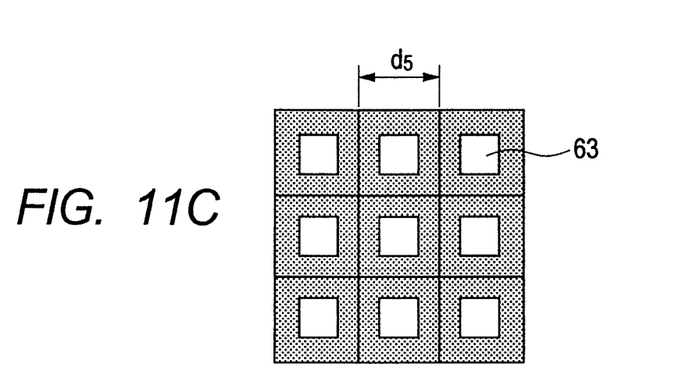
FIG. 11C is a diagram for describing a masking grating in Example 3.

FIG. 11C is a view of a part of the masking grating in the present example seen from the side of the X-ray source. In the masking grating which is made of gold similarly to Example 1, transmitting portions 63 for transmitting X-rays and masking portions 64 for masking the X-rays are arranged in a mesh pattern with the same period $d_5$ as the period of the interference pattern. The transmitting portion 63 has a square shape having one side of $d_5/2$.

As can be seen from comparison of from FIG. 11B and FIG. 11C with FIG. 3 and FIG. 4, the interference pattern and the masking grating of the present example are the same as those of example 1, and hence the overlapping state of the interference pattern and the masking grating, and the relationship between the movement of the diffraction grating and the amount of X-rays transmitted through the transmitting portion 63 of the masking grating are also the same as those of Example 1. The measurement steps in the present example are the same as those in Example 1 described with reference to FIG. 7, and hence the description thereof is omitted.

Further, the pattern of the diffraction grating and the pattern of the masking grating can also be exchanged with each other. That is, it may also be configured such that the diffraction grating has the mesh pattern as illustrated in FIG. 11C, and such that the masking grating has the checker pattern as illustrated in FIG. 11A. In this case, an interference pattern as illustrated in FIG. 8B is obtained. When the diffraction grating and the masking grating configured as described above are used, the interference pattern and the masking grating are the same as those of Example 2. Thus, the overlapping state of the bright zones of the interference pattern and the transmitting portions 63 of the masking grating, and the relationship between the movement of the diffraction grating and the amount of X-rays transmitted through the transmitting portions 63 of the masking grating are also the same as those of Example 2.

In the above, the exemplary embodiment of the present invention has been described. However, the present invention is not limited to the above-described embodiment but various changes and modifications are possible without departing from the spirit and scope of the present invention. Accordingly, the following claims are appended to disclose the scope of the present invention. This application claims the benefit of priority from Japanese Patent Application No. 2010-121225 filed in Japan on May 27, 2010, the entire content of which is hereby incorporated by reference in this application.

Industrial Applicability

The present invention can be used for an imaging apparatus for imaging a subject, which apparatus uses the phase change produced when X-rays are transmitted through the subject.

REFERENCE SIGNS LIST

1 X-ray source
2 X-ray
3 Subject
4 Diffraction grating
5 Moving device for diffraction grating
6 Masking grating
7 Moving device for masking grating
8 Detector
9 Calculator While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-121225, filed May 27, 2010, which is hereby incorporated by reference herein in its entirety.

The invention claimed is:
1. An X-ray imaging apparatus comprising:
a diffraction grating which diffracts X-rays emitted from an X-ray source to thereby form an interference pattern having two-dimensionally arranged bright and dark zones;
a masking grating in which masking portions for masking the X-rays and transmitting portions for transmitting the X-rays are two-dimensionally arranged to partially mask each of the bright zones of the interference pattern;
a moving device which changes the relative position between said interference pattern and said masking grating;
a detector which detects an intensity distribution of the X-rays transmitted through said masking grating; and
a calculator which calculates a differential phase contrast image or a phase contrast image of a subject on the basis of the result of detection performed by said detector, said calculator being configured to calculate the differential phase contrast image or the phase contrast image in each of two mutually crossing directions on the basis of results of detections performed a plurality of times by said detector
wherein a plurality of the results of detection performed by said detector are used to calculate the differential phase contrast image or the phase contrast image in each of the two mutually crossing directions.

2. The X-ray imaging apparatus according to claim 1,
wherein said moving device changes the relative position in the two directions crossing each other, and
wherein said detector detects, a plurality of times, the intensity distribution of the X-rays in correspondence with the change of the relative position to thereby acquire the results of the plurality of times of detections.

3. The X-ray imaging apparatus according to claim 1, wherein said moving device moves at least one of said X-ray source, said diffraction grating, and said masking grating.

4. The X-ray imaging apparatus according to claim 2,
wherein said moving device changes the relative position in two directions orthogonal to each other, and
wherein said calculator calculates a differential phase contrast image or a phase contrast image in each of the two directions orthogonal to each other.

5. The X-ray imaging apparatus according to claim 1,
wherein said diffraction grating has phase advance portions and phase lag portions, the phase difference between an X-ray transmitted through one of said phase advance portions and an X-ray transmitted through one of said phase lag portions being $\pi/2$, and said phase advance portions and said phase lag portions being arranged in a checker pattern, and
wherein said masking grating has said masking portions and said transmitting portions arranged in a mesh pattern.

6. The X-ray imaging apparatus according to claim 1,
wherein said diffraction grating has phase advance portions and phase lag portions, the phase difference between an X-ray transmitted through one of said phase advance portions and an X-ray transmitted through one of said phase lag portions being $\pi$, and said phase advance portions and said phase lag portions being arranged in a checker pattern, and
wherein said masking grating has said masking portions and said transmitting portions arranged in a checker pattern.

7. The X-ray imaging apparatus according to claim 1,
wherein said diffraction grating has transmitting portions for transmitting X-rays and masking portions for masking X-rays, said transmitting portions and said masking portions of said diffraction grating being arranged in a checker pattern, and
wherein said masking grating has said masking portions and said transmitting portions arranged in a mesh pattern.

8. The X-ray imaging apparatus according to claim 1, wherein said diffraction grating has transmitting portions for transmitting X-rays and masking portions for masking X-rays, said transmitting portions and said masking portions of said diffraction grating being arranged in a mesh pattern, and
wherein said masking grating has said masking portions and said transmitting portions arranged in a checker pattern.

9. An X-ray imaging apparatus comprising:
a diffraction grating which diffracts X-rays emitted from an X-ray source to thereby form an interference pattern having two-dimensionally arranged bright and dark zones;
a masking grating in which masking portions for masking the X-rays and transmitting portions for transmitting the X-rays are two-dimensionally arranged to partially mask each of the bright zones of the interference pattern;
a moving device which changes the relative position between said interference pattern and said masking grating;
a detector which detects an intensity distribution of the X-rays transmitted through said masking grating; and
a calculator which calculates a differential phase contrast image or a phase contrast image of a subject on the basis of the result of detection performed by said detector, said calculator being configured to calculate the differential phase contrast image or the phase contrast image in each of two mutually crossing directions on the basis of results of detections performed a plurality of detector,
wherein the bright and dark zones of the interference pattern are arranged in a checker pattern, and said masking portions and said transmitting portions of said masking grating are arranged in a mesh pattern, and a direction of the arrangement of the interference pattern and a direction of the arrangement of said masking grating are different by 45 degrees from each other.

10. An X-ray imaging apparatus comprising:
a diffraction grating which diffracts X-rays emitted from an X-ray source to thereby form an interference pattern having two-dimensionally arranged bright and dark zones;
a masking grating in which masking portions for masking the X-rays and transmitting portions for transmitting the X-rays are two-dimensionally arranged to partially mask each of the bright zones of the interference pattern;
a moving device which changes the relative position between said interference pattern and said masking grating;
a detector which detects an intensity distribution of the X-rays transmitted through said masking grating; and
a calculator which calculates a differential phase contrast image or a phase contrast image of a subject on the basis of the result of detection performed by said detector, said calculator being configured to calculate the differential phase contrast image or the phase contrast image in each of two mutually crossing directions on the basis of results of detections performed a plurality of times by said detector,
wherein the bright and dark zones of the interference pattern are arranged in a mesh pattern, and said masking portions and said transmitting portions of said masking grating are arranged in a checker pattern, and a direction of the arrangement of the interference pattern and a direction of the arrangement of said masking grating are different by 45 degrees from each other.

11. The X-ray imaging apparatus according to claim 1,
wherein said moving device changes the relative position in the two directions crossing each other,
wherein said detector detects, an odd number of times, the intensity distribution of the X-rays in correspondence with the change of the relative position to thereby acquire the results of the odd number of times of detections, and
wherein said calculator calculates the differential phase contrast image or the phase contrast image in each of the two mutually crossing directions on the basis of results of the detection performed the odd number of times by said detector.

12. The X-ray imaging apparatus according to claim 1,
wherein said moving device changes the relative position in the two directions crossing each other,
wherein said detector detects, five times, the intensity distribution of the X-rays in correspondence with the change of the relative position to thereby acquire the results of the five times of detections, and wherein said calculator calculates the differential phase contrast image or the phase contrast image in each of the two mutually crossing directions on the basis of results of the detections performed five times by said detector.

* * * * *